(12) United States Patent
WasDyke

(10) Patent No.: US 8,080,033 B2
(45) Date of Patent: Dec. 20, 2011

(54) STAGED RELEASE OF IVC FILTER LEGS

(75) Inventor: Joel M. WasDyke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 197 days.

(21) Appl. No.: 12/490,761

(22) Filed: Jun. 24, 2009

(65) Prior Publication Data

US 2009/0264915 A1  Oct. 22, 2009

Related U.S. Application Data

(62) Division of application No. 10/280,181, filed on Oct. 25, 2002, now abandoned.

(51) Int. Cl.
*A61M 29/00* (2006.01)
(52) U.S. Cl. ......................................................... 606/200
(58) Field of Classification Search .................. 606/200; 604/264, 523; 600/585; 128/830, 831
See application file for complete search history.

(56) References Cited

U.S. PATENT DOCUMENTS

| | | | |
|---|---|---|---|
| 3,952,747 A | 4/1976 | Kimmell, Jr. | |
| 4,688,553 A | 8/1987 | Metals | |
| 4,793,348 A | 12/1988 | Palmaz | |
| 4,873,978 A | 10/1989 | Ginsburg | |
| 5,059,205 A | 10/1991 | El-Nounou et al. | |
| 5,329,942 A | 7/1994 | Gunther et al. | |
| 5,421,832 A | 6/1995 | Lefebvre | |
| 5,634,942 A * | 6/1997 | Chevillon et al. | 606/200 |
| 5,681,347 A | 10/1997 | Cathcart et al. | |
| 5,813,405 A | 9/1998 | Montano et al. | |
| 5,893,869 A | 4/1999 | Barnhart et al. | |
| 5,951,585 A | 9/1999 | Cathcart et al. | |
| 6,027,518 A | 2/2000 | Gaber | |
| 6,146,404 A | 11/2000 | Kim et al. | |
| 6,165,179 A | 12/2000 | Cathcart et al. | |
| 6,165,200 A | 12/2000 | Tsugita et al. | |
| 6,383,193 B1 | 5/2002 | Cathcart et al. | |
| 6,440,077 B1 | 8/2002 | Jung et al. | |
| 6,596,011 B2 | 7/2003 | Johnson et al. | |
| 2001/0020175 A1 | 9/2001 | Yassour et al. | |
| 2002/0032461 A1 | 3/2002 | Marshall | |
| 2002/0042626 A1 | 4/2002 | Hanson et al. | |

FOREIGN PATENT DOCUMENTS

EP       0678284 A1    4/1995

* cited by examiner

*Primary Examiner* — Julian Woo
(74) *Attorney, Agent, or Firm* — Seager, Tufte & Wickhem LLC

(57) ABSTRACT

A catheter for stage-delivering a vena cava filter within a body lumen is disclosed. The catheter may comprise an elongated tubular member having a proximal section, a distal section, and an inner lumen configured to receive an intravascular filter. One or more notches or slits radially disposed about the distal end of the catheter may be utilized to stage-deploy the filter within the body. Several grooves or indentations disposed along an inner surface of the catheter may also be employed.

7 Claims, 2 Drawing Sheets

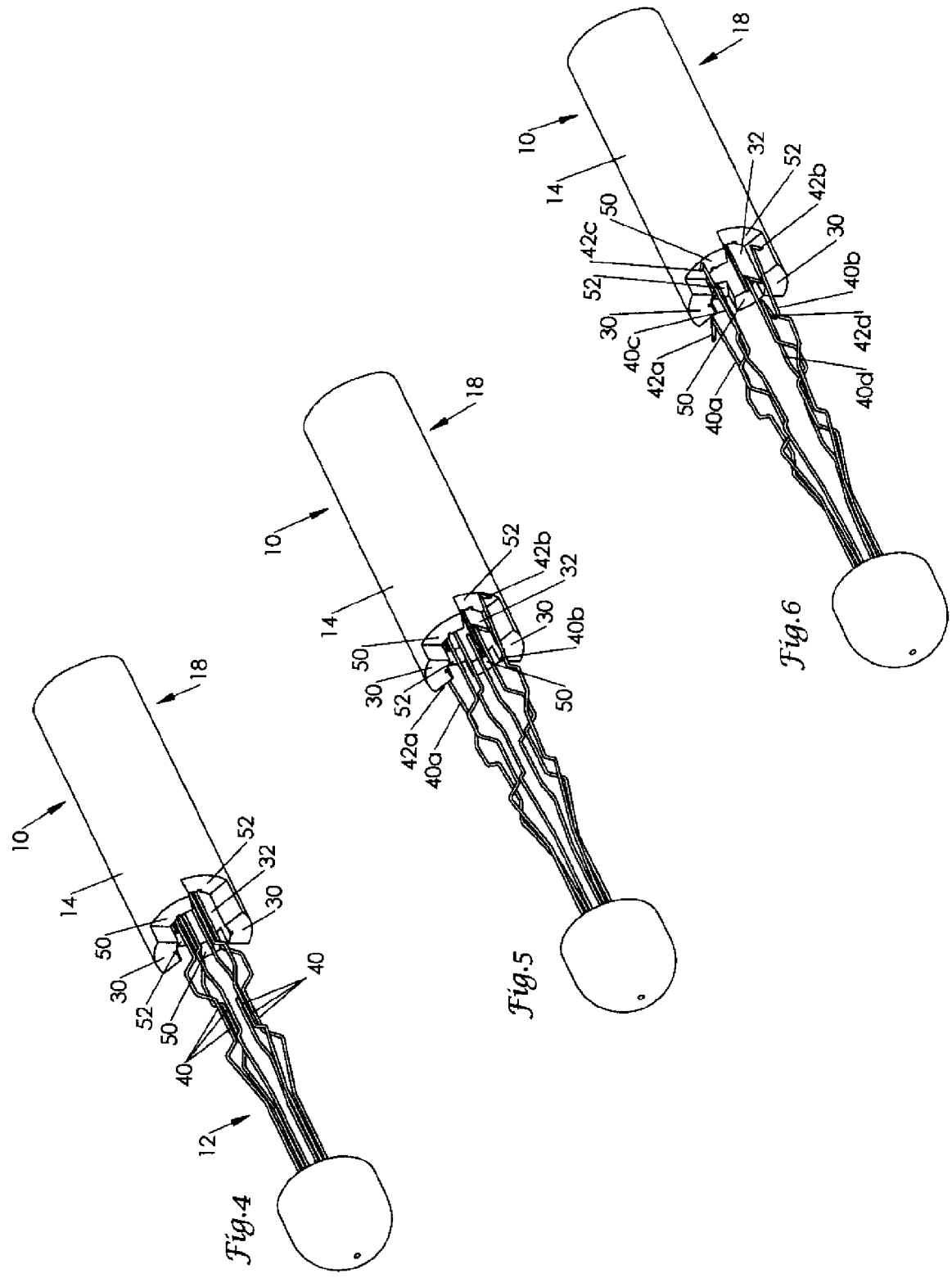

STAGED RELEASE OF IVC FILTER LEGS

RELATED APPLICATIONS

This application is a divisional application of U.S. application Ser. No. 10/280,181 filed Oct. 25, 2002 now abandoned.

FIELD OF THE INVENTION

The present invention relates generally to the field of vena cava filters. More specifically, the present invention pertains to devices for delivering vena cava filters within the body.

BACKGROUND OF THE INVENTION

Vena cava filters are typically used in combination with other thrombolytic agents to treat pulmonary embolism occurring within a patient. These devices are generally implanted within a vessel such as the inferior vena cava, and function by capturing blood clots (emboli) contained in the blood stream before they can reach the lungs and cause permanent damage to the patient. To trap emboli contained within the blood, many conventional vena cava filters utilize a plurality of independent filter legs that can be expanded within the body to form a conical-shaped surface that captures blood clots without disturbing the flow of blood. Once collected, a natural clot lysing process occurs within the body to dissolve the blood clots collected by the filter.

Delivery of the vena cava filter within the body is generally accomplished via an introducer catheter or sheath percutaneously inserted through the femoral (groin) or jugular (neck) veins. Such introducer catheters or sheaths are generally tubular in shape, and include an inner lumen configured to transport the filter in a collapsed position through the body. Once transported to a desired location in the body (e.g. the inferior vena cava), the filter can then be removed from within the catheter or sheath, allowing the filter legs to spring open and engage the vessel wall. A hook, barb or other piercing means disposed on the base of each filter leg can be used to secure the filter to the vessel wall.

The efficacy of vena cava filters is dependent on several factors, including the dimensions of the vena cava, and the alignment of the filter legs when the device is launched within the body. Since many introducer catheters deploy the filter legs simultaneously in a single step, the spring force resulting from the deployment of the filter legs within the vessel may cause the filter to displace from its intended placement position. In some cases, the hooks on the ends of the filter legs may also interfere with each other, causing the filter to asymmetrically deploy within the body.

SUMMARY OF THE INVENTION

The present invention relates to devices for delivering vena cava filters within the body. In an exemplary embodiment of the present invention, a delivery catheter may comprise a proximal section, a distal section, and an inner lumen configured to receive a vena cava filter. The vena cava filter may include an apical head coupled to a plurality of expandable filter legs. Each filter leg may include a bend region that allows the filter to bend or flex when radially unconstrained, and a hook region to fix the filter to the vessel wall. A push member slidably disposed within the inner lumen of the catheter can be used to eject the filter from the catheter.

One or more notches or slits radially disposed about the distal end of the catheter may be utilized to stage-deploy the vena cava filter within the body. The notches or slits may be formed at differing depths and at various locations about the distal end of the catheter, depending on the type of vena cava filter employed. In one exemplary embodiment, a first and second set of opposing notches or slits may be formed about the distal end of the catheter. The second set of opposing notches or slits may be formed adjacent to and at a depth greater than the first set of notches or slits, forming a crenellated surface about the distal end of the catheter. In use, the push member can be used to eject the filter legs in various stages.

In certain embodiments, the catheter may further include one or more grooves or indentations formed along the inner surface of the distal section. The grooves or indentations are radially aligned with each of the notches or slits, and are configured to slidably receive the hook region on each filter leg. In use, the grooves or indentations ensure proper radial alignment of the filter legs within the inner lumen, and prevent leg crossing as the filter legs eject from the catheter.

BRIEF DESCRIPTION OF THE DRAWINGS

FIG. 4 is a perspective view of the catheter illustrated in FIG. 1, wherein the filter legs are shown withdrawn slightly from the distal end of the catheter;

FIG. 5 is a perspective view of the catheter illustrated in FIG. 1, wherein the vena cava filter is shown in a second position with a first set of filter legs ejected from the catheter; and FIG. 6 is a perspective view of the catheter illustrated in FIG. 1, wherein the vena cava filter is shown in a third position with a second set of filter legs ejected from the catheter.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
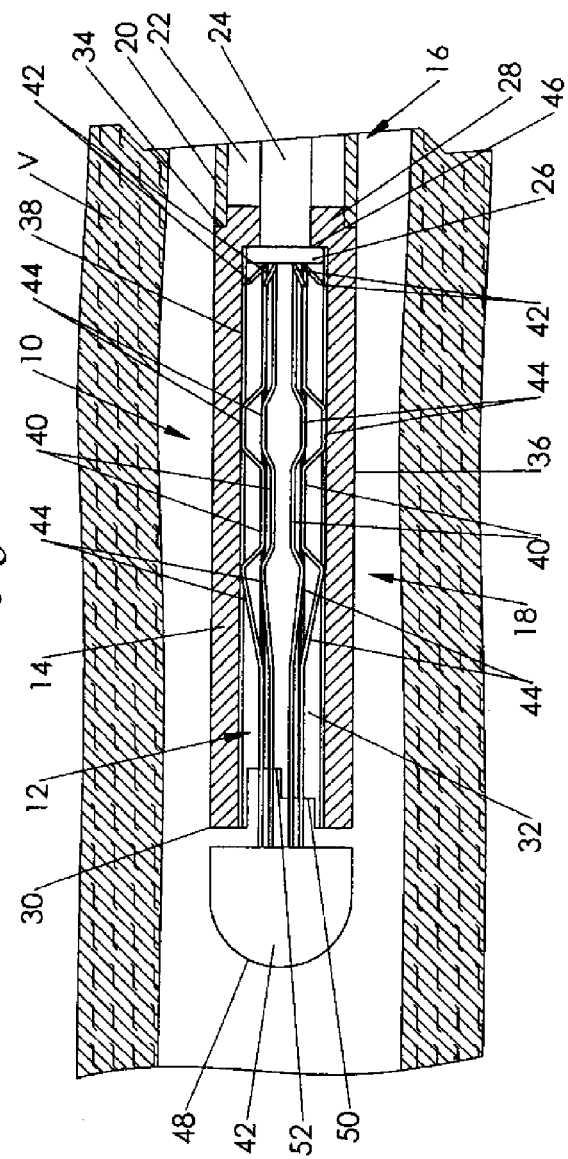
FIG. 1 is a partial cross-sectional view of the distal portion of a catheter in accordance with an exemplary embodiment of the present invention, wherein a vena cava filter is shown fully loaded within the catheter.

FIG. 1 is a partial cross-sectional view of the distal section of a catheter 10 in accordance with an exemplary embodiment of the present invention, showing a vena cava filter 12 fully loaded within the catheter. Catheter 10 is formed of an elongated tubular member 14 having a proximal section 16 and a distal section 18. In the particular view illustrated in FIG. 1 the distal section 18 of catheter 10 is shown advanced to a desired location within a vessel V, such as the inferior vena cava.

The proximal section 16 of catheter 10 is formed from an axially stiff radially flexible hypodermic tube having a proximal end (not shown) and a distal end 20. The proximal section 16 defines an inner lumen 22 configured to slidably receive a push member 24 that can be manipulated by the physician at the proximal end of the catheter 10 to eject the filter 12 from the catheter 10 and into the vessel V. The push member 24 comprises an axially stiff, radially flexible tubular member formed of a suitable metal or polymeric material with an annular-shaped disk 26 formed at the distal end thereof.

The distal section 18 of catheter 10 is formed of a stainless steel hypodermic tube 14 having a proximal end 28, a distal end 30, and an inner lumen 32 configured to contain the filter 12 in a collapsed position. The proximal end 28 of distal section 18 is attached to the distal end 20 of the proximal section 16 at joint 34. Attachment of the proximal end 28 of the distal section 18 to the distal end 20 of the proximal section 16 can be accomplished by any number of suitable joining methods, including adhesion bonding, ultrasonic welding, rf welding, crimping, soldering, brazing, or any combination thereof.

The proximal and distal sections 16, 18 are dimensioned such that the profile of the catheter 10 is substantially uniform along the entire length of the catheter 10. A lubricious (e.g. hydrophilic) coating may be placed on the outer surface 36 of the catheter 10 to facilitate insertion and advancement of the catheter 10 within the vessel V. Moreover, the inner surface 38 of the distal section 18 may be polished, buffed, or deburred to provide a smoothly bored surface to reduce the frictional force exerted on the filter 12 by the catheter 10 when ejected from the inner lumen 32.

As shown in FIG. 1, vena cava filter 12 includes a plurality of filter legs 40 coupled to an apical head 42. Each of the filter legs 40 may include a radially extending hook region 42 comprising a hook, barb or other piercing means formed on the proximal end of each filter leg 40. Moreover, each of the filter legs 40 may include one or more bend regions 44 that impart flexibility to the filter 12. In the particular position depicted in FIG. 1, the filter legs 40 are shown fully loaded within the inner lumen 32 such that the hook regions 42 are disposed at or near the proximal end 28 of the distal section 18. The remainder of the filter 12 extends distally along the length of the distal section 18 with a portion extending beyond the distal end 30.

The annular-shaped disk 26 on the distal end of the push member 24 acts as a proximal stop for the filter 12 when loaded into the distal section 18 of the catheter 10, and is configured to engage the hook regions 42 when filter 12 is deployed within vessel V. The annular-shaped disk 26 has an outer diameter that is slightly smaller than the inner diameter of the elongated tubular member 14, allowing the disk 26 to be advanced between the proximal and distal ends 28, 30 of the distal section 18. A shoulder 46 on the proximal end 28 of the distal section 18 confines the annular-shaped disk 26 proximally.

In the exemplary embodiment illustrated in FIG. 1, filter 12 is front-loaded into the distal section 18 of catheter 10 such that the apical head 42 portion of the filter 12 extends distally beyond the distal end 30, and the hook region 42 of each filter leg 40 lie flush with the annular-shaped disk 26. In a front-loaded position, filter 12 can be inserted and delivered percutaneously through a femoral artery located near the patient's groin. The apical head 42 may have a profile substantially similar to the profile of the catheter 10, and may include a rounded, atraumatic distal portion 48. As with the outer surface 36 of catheter 10, the apical head 42 may be formed of or coated with a lubricious material. The apical head 42 and/or filter legs 40 may also be coated with an anti-thrombogenic agent such as heparin (or its derivatives), urokinase, or PPack (dextrophenylalanine proline arginine chloromethylketone), if desired.

In an alternative embodiment, filter 12 can be back-loaded into the distal section 18 of catheter 10 to permit placement of the filter 12 via a jugular approach (i.e. through the jugular vein). Apical head 42 can be dimensioned to slidably fit within the inner lumen 32 of distal section 18. To back-load the filter 12 into the catheter 10, the apical head 42 is first inserted into inner lumen 32, followed by the filter legs 40 and hook regions 42. The distal section 18 can be dimensioned such that, when filter 12 is fully loaded into inner lumen 32, the hook regions 42 do not extend beyond the distal end 30 of the catheter 10. In use, the catheter 10 and enclosed filter 12 can be inserted percutaneously into the jugular vein, and advanced to a desired location within the body. The push member 24 can then be actuated to eject the filter legs 40 from inner lumen 32. Ejection of the filter legs 40 from the inner lumen 32 causes the filter legs 40 to expand and engage the vessel wall.

Figure 2:
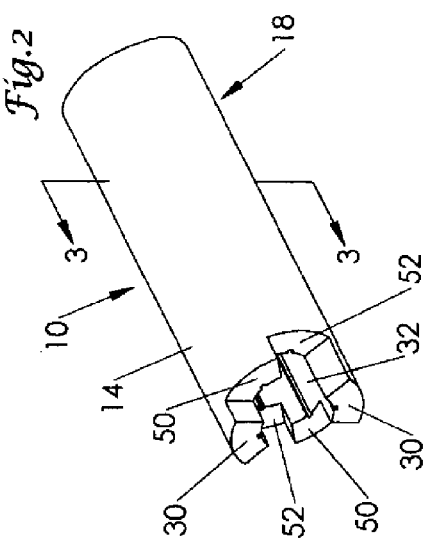
FIG. 2 is a perspective view of the catheter illustrated in FIG. 1.

FIG. 2 is a perspective view of the catheter 10 illustrated in FIG. 1, wherein the filter 12 has been removed to show two sets of notches or slits 50, 52 formed at the distal end 30 of the distal section 18. The first set of notches or slits 50 are formed by removing a portion of the elongated tubular member 14 at the distal end 30. The first set of notches or slits 50 may be radially spaced 180° apart from each other in an opposing manner. The second set of notches or slits 52 are likewise formed by removing another portion of the elongated tubular member 14 at the distal end 30, but at a greater depth such that the second set of notches or slits 52 extend proximal the first set of notches or slits 50. As can be seen from FIG. 1, the first and second set of notches 50, 52 extend proximally from the distal end 30 of the catheter 10, and are located adjacent to each other to form a crenellated surface.

Figure 3:
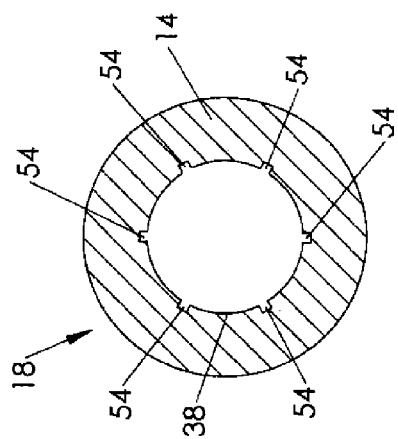
FIG. 3 is a cross-sectional view of the catheter illustrated in FIG. 2 along line 3-3, showing the location of the grooves or indentations within the inner surface of the distal section.

Catheter 10 may further include several grooves or indentations 54 formed in the inner surface 38 of the elongated tubular member 14. As shown in FIG. 3, for example, six grooves or indentations 54 may be formed at equidistant intervals about the inner surface 38 of the elongated tubular member 14. The grooves or indentations 48 extend distally along the length of the elongated tubular member 14 from the shoulder 46 to the distal end 28, and are radially aligned with each of the notches or slits 50, 52. The grooves or indentations 54 are configured to slidably receive the hook region 42 on each filter leg 40. In use, the grooves or indentations 54 ensure proper radial alignment of the filter legs 40 within the inner lumen 32, and prevent leg crossing as the filter legs 40 are ejected from the catheter 10.

Referring now to FIGS. 4-6, a method of stage-deploying an intravascular filter from a catheter will now be described in the context of the vena cava filter 12 and catheter 10 described above. In a first position shown in FIG. 4, catheter 10 has been withdrawn slightly such that the filter legs 40 are partially removed from within the inner lumen 32. Withdrawal of the filter 12 from within lumen 32 can be accomplished by retracting the elongated tubular member 14 proximally while holding the push member 24 stationary, or in the alternative, holding the elongated tubular member 14 stationary while advancing the push member 24 distally. A radiopaque marker band or other measuring means (not shown) may be placed on the catheter 10 and/or filter 12 to determine the precise location of the filter 12 within the vessel.

As the operator continues to withdraw the filter 12 from the catheter 10, the hook regions 42a, 42b on a first set of filter legs 40a, 40b radially aligned with the second set of notches or slits 52 eject from the inner lumen 32, allowing the filter legs 40a, 40b to expand, as shown in FIG. 5. Once expanded, the hook regions 42a, 42b on the first set of filter legs 40a, 40b lock onto the vessel wall, fixing the location of the filter 12 within the vessel. Continued retraction of the catheter 10 proximally to a second position causes a second set of filter legs 40c, 40d aligned with the first set of notches or slits 50 to eject from the inner lumen 32, allowing the second set of filter legs 40c, 40d to expand and engage the vessel wall, as shown in FIG. 6. Further retraction of the catheter 10 proximally to a third position causes the third and final set of filter legs to eject from the inner lumen 32 and expand in like fashion. By stage-deploying the filter legs 40 from the catheter 10, the operator can lock the filter 12 to a particular location along the vessel wall prior to full fixation of the device within the vessel.

The number and alignment of the notches or slits disposed about the catheter can be selected to accommodate different types of intravascular devices. For example, a catheter in accordance with an exemplary embodiment of the present invention may include eight notches or slits radially disposed at various depths and angles about the distal end of the catheter. In use, the catheter can be utilized to stage-deploy an intravascular device (e.g. a vena cava filter) having eight filter legs, similar to that described above with respect to FIGS. 4-6.

Although FIGS. 4-6 shows the stage-deployment of a vena cava filter having three sets of opposing filter legs, it should be understood that other configurations are possible without deviating from the scope of the invention. The catheter may be adapted to deploy each filter leg independently at each stage, or multiple filter legs at each stage. For example, a catheter adapted to stage-deploy an intravascular filter may include a group of three notches or slits radially spaced 120° apart from each other. An intravascular filter having two sets of three filter legs radially disposed 120° apart from each other may be stage-deployed in a two-step process wherein a first group of three filter legs are first ejected through a notched portion on the catheter, followed by the remaining filter legs from the distal end of the catheter.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A catheter, comprising:
   an elongated tubular member having a proximal section, a distal section, and an inner lumen;
   an intravascular filter disposed within the lumen;
   a first set and a second set of notches or slits radially disposed about the distal end of said distal section, said first set of notches or slits extending proximally from the distal end of the elongated tubular member, said second set of notches or slits extending proximally from the distal end of the elongated tubular member to a greater depth than the first set of notches or slits, said first and second sets of notches or slits being located adjacent to each other to form a crenellated surface, said first and second sets of notches or slits being radially disposed at equidistant intervals about the distal end of said distal section; and
   one or more grooves or indentations formed along an inner surface of the distal section, said one or more grooves or indentations corresponding in number and arrangement with said first and second sets of notches or slits, each of the one or more grooves or indentations being radially aligned with a corresponding one of the first and second sets of notches or slits.

2. The catheter of claim 1, wherein said first and second sets of notches or slits comprise two sets of opposing notches.

3. The catheter of claim 1, wherein said intravascular filter is a vena cava filter.

4. The catheter of claim 3, wherein said vena cava filter is front-loaded into the catheter for placement through a femoral artery.

5. The catheter of claim 3, wherein said vena cava filter is back-loaded into the catheter for placement through the jugular vein.

6. The catheter of claim 3, wherein said vena cava filter includes a plurality of expandable filter legs coupled to an apical head.

7. The catheter of claim 6, wherein each of said plurality of expandable filter legs includes a hook region.

* * * * *